United States Patent [19]

Lemonnier

[11] Patent Number: 4,902,415

[45] Date of Patent: Feb. 20, 1990

[54] FILTRATION ASSEMBLY FOR PERIDURAL ANESTHESIA

[75] Inventor: Jean Lemonnier, Le Vesinet, France

[73] Assignee: Millipore Corporation, Bedford, Mass.

[21] Appl. No.: 221,148

[22] Filed: Jul. 19, 1988

[30] Foreign Application Priority Data

Jul. 23, 1987 [FR] France ................... 87 10479

[51] Int. Cl.⁴ ............................................ B01D 13/00
[52] U.S. Cl. ............................. 210/321.84; 210/445; 210/447
[58] Field of Search ............... 210/446, 447, 445, 450, 210/232, 321.84

[56] References Cited

U.S. PATENT DOCUMENTS 4,422,939 12/1983 Sharp et al. ............ 210/447 X
4,690,757 9/1987 Mathus et al. ........... 210/446 X Primary Examiner—Frank Spear
Attorney, Agent, or Firm—Andrew T. Karnakis; Paul J. Cook

[57] ABSTRACT

A filtration apparatus suitable for use in peridural anesthesia formed of two mating sections and a membrane positioned between and supported by the sections. Each section has an liquid inlet or liquid outlet and are joined together to form a chamber therebetween. The membrane is positioned at an angle between about 5° and 15° relative to the axes of the inlet and outlet.

11 Claims, 3 Drawing Sheets

FILTRATION ASSEMBLY FOR PERIDURAL ANESTHESIA

BACKGROUND OF THE INVENTION

The present invention relates to a filtration apparatus useful for peridural or epidural anesthesia. Peridural or epidural anesthesia are a type of locoregional anesthesia currently used in treating pain, especially for chronic illnesses, surgical operations and childbirth. In this procedure, the practitioner should first locate the peridural space, where the spinal nerve to be anesthetized is found, by introducing the end of a bevelled peridural needle upward between the second and third lumbar vertebrae. This beveled end emerges into the peridural space deliminated by the dura matter and the walls of the spinal canal. A flexible catheter then is introduced through this needle, in order to deliver the anesthetic into the space.

In order to avoid any bacterial and microparticular (glass, rubber, etc.) contamination arising from the transfer of the anesthetic, it is imperative to effect a filtration through a device located downstream from the syringe delivering the anesthetic and upstream from the catheter.

At the present time, two different filter assemblies for peridural anesthesia are available. A first type consists of a circular filtering membrane, the periphery of which is joined to an envelope of plastic material in two parts, located on either side of the membrane; each of these two parts has an enclosed space equipped with an inlet or outlet opening. The axis of the enclosed space is perpendicular to the plane of the filtering membrane. This first type of filter is not suitable in practice due to its structure having a top surface which prevents it fixation in a convenient and comfortable manner to the body of the patient being treated.

A second type of filter differs from the first type in that the axes of the inlet and outlet orifices to spaces located on either side of the filtering membrane are arranged, not perpendicularly, but in parallel to the plane of this membrane; itself parallel to the filtration case. However, in this second filter type the inlet and outlet openings project from the same side of the membrane, which presents a double disadvantage. Such an arrangement permits fixing the filter on the body of the patient on only one side, i.e., the side opposite that from which the access openings to the membrane project. Also, because the two openings are located on the same side of the membrane, a "U" shaped access channel to the opposite side of the membrane must be provided for one of them which necessitates the presence of a third, circular crown-shaped plastic element in order to delimit this access channel. A structure with three plastic elements increases the cost of manufacturing this filter type and, furthermore, due to the U-shape of the access channel to one of the sides of the membranes, creates a pressure drop that reduces the sensitivity of the apparatus during use by the anesthetist.

SUMMARY OF THE INVENTION

In accordance with this invention, a flat reversible filtration assembly for particular application in peridural anesthesia is comprised of an envelope of only two sections, joined to each other and positioned on either side of a filtering membrane. Each section has an inlet or outlet hole that communicates with a chamber having membrane support elements.

The filtration assembly of this invention is characterized by the membrane support elements of each of the two sections having a circular support surface that forms an acute angle with respect to the axes of the inlet and outlet holes and that one of the surfaces of the support surfaces is devoid of any projection beyond that surface. Because of the inclination of the filtration membrane, the access orifices located on either side of the membrane can be placed on the filtration assembly without their projecting beyond the ends of the membrane. Such a structure assures a perfect reversibility of the filtration assembly, which can be placed with either side directly on the body of the patient, which eliminates positioning errors. On the other hand, the fact that one of the surfaces of the membrane support provided in one of the two sections has no portion that projects beyond this surface makes it possible to join the membrane on this surface by means of an automatic device from a continuous strip of filtering material from which the membrane is cut.

Finally, the circular form of the surfaces of the filtering memberane support and the inclination of the membrane with respect to the direction of displacement of the filtered liquid make it possible to avoid the formation of an air pocket, a generator of bubbles that can cause undesirable perturbations in the fluid flow after its passage in the filtration assembly of the invention.

DESCRIPTION OF THE DRAWING

The present invention will now be described in a particular implementation that is illustrated by the attached drawings in which.

Figure 5:
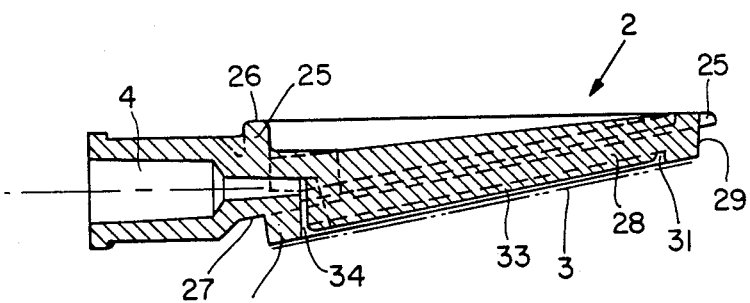
Figure 6:
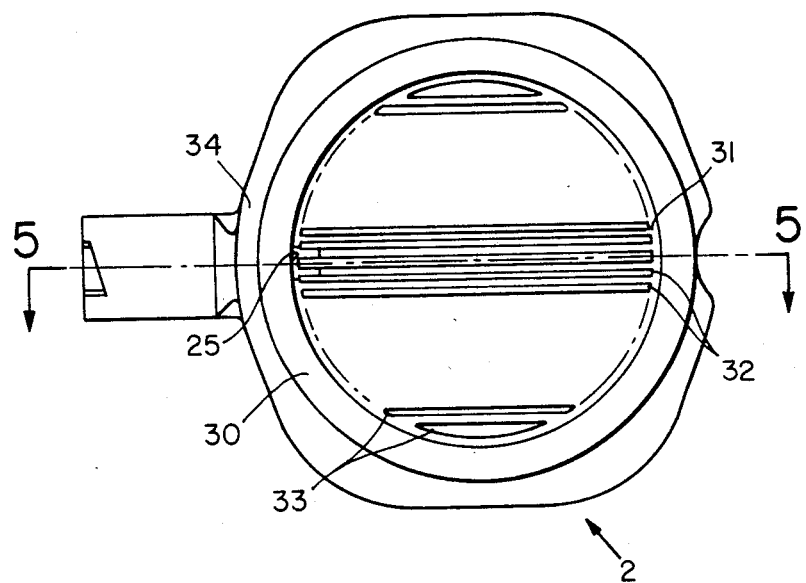

The FIGS. 5 and 6 respectively show a cutaway view along the line 5—5 of FIG. 6 with filtering membrane and a bottom view without filtering assembly according to the invention.

DESCRIPTION OF SPECIFIC EMBODIMENTS

Figure 1:
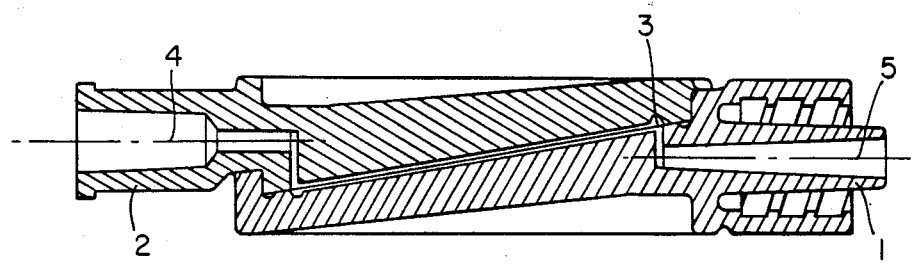
FIG. 1 shows a cutaway view along line 1—1 of FIG. 2 of the filtration assembly according to the invention.
Figure 2:
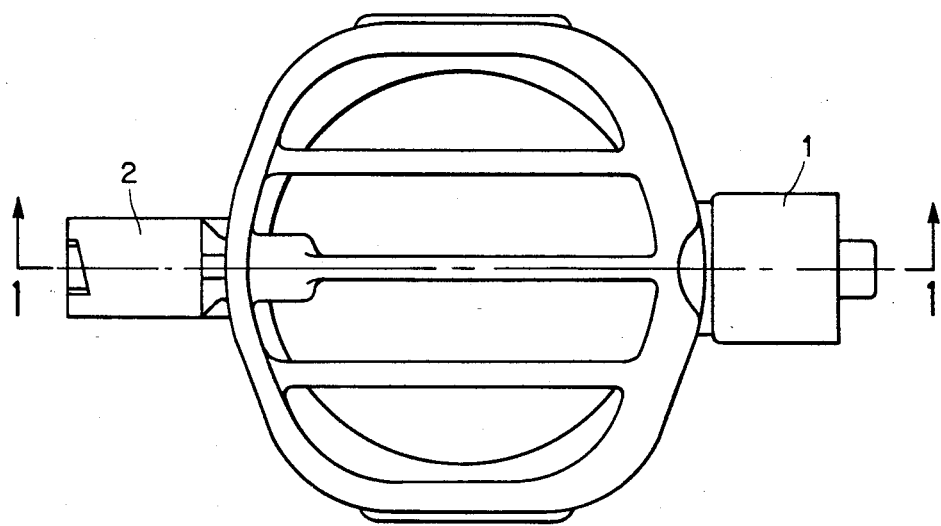
FIG. 2 shows a top view of the device of FIG. 1.

The filtration assembly for peridural anesthesia shown in FIGS. 1 and 2 has an envelope in two sections 1 and 2, between which a filtering membrane 3 is located. The lower section of base 1 is shown in FIGS. 3 and 4 and the upper section or cover 2 is shown in FIGS. 5 and 6.

Figure 3:
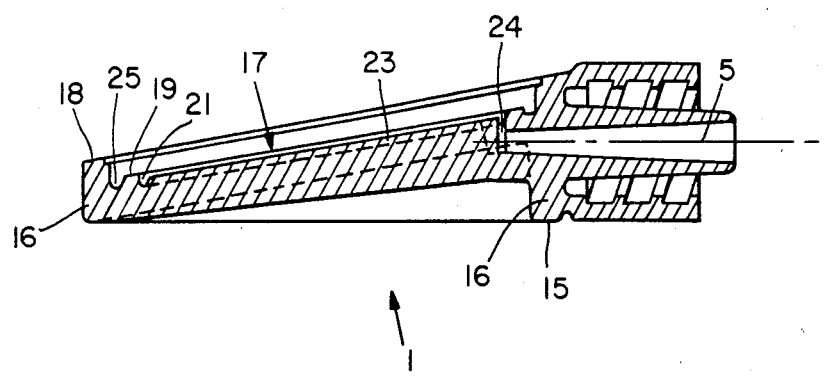
FIGS. 3 and 4 respectively show a cutaway view along line 3—3 of FIG. 4 and a top view of the lower section of the envelope.
Figure 4:
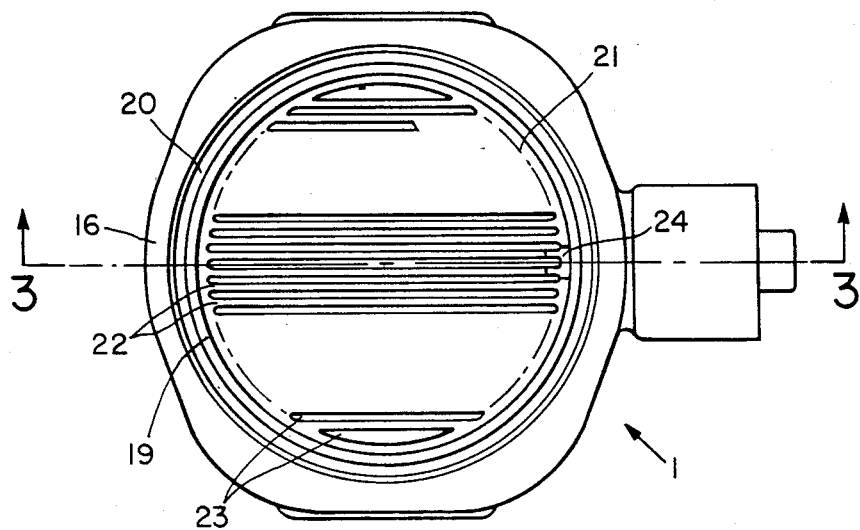

As illustrated more particularly in FIG. 3, the base 1 has an essentially cylindrical vertical wall 16 that has a lower end 15 in a horizontal plane and an upper end 18 located in a plane that forms an acute angle with respect to the horizontal. This angle is preferably between 5 and 15° and is preferably equal to about 10° in the example shown in FIGS. 1-6. The base 1 also has a bottom 17, the plane of which forms the same acute angle as that of the upper end 18 of the wall 16 so as to form a female element. The upper face of the bottom 17, which is an inclined plane, has a plane peripheral crown 19 delimited by an external circular throat 20 and an internal, also circular throat 21. The totality of the surface located inside of the plane crown 19 so as to form an inclined surface of the lower support of the filtering membrane 3.

The base 1 also has an outlet hole 5 having an axis, as shown in FIG. 3, parallel to the plane of the lower end 15 and which is conical with double external threads so as to form a conventional luer-type connection for the catheter. This hole 5 passes through the wall 16 and communicates at right angles with a feed channel 24 that empties directly in the circular internal throat 21. This feed channel 24 preferably has a straight U-shaped section (see FIG. 4) in which the base of the "U" empties into the throat 21 and the two branches of the "U", the length of which can increase as the said section approaches the throat 21, empty into two parallel longitudinal grooves or slots 22.

The upper section or cover 2 of the filtration assembly according to the invention has, as shown in FIG. 5, a vertical wall 25 that has a plane upper end 26 located in a horizontal plane and a lower end 7 located in a plane that forms the same acute angle with respect to the horizontal as that of the base 1. The cover 2 also has a bottom 28, the plane of which forms the same acute angle as that of the lower end 27 of the wall 25 and which is connected to the latter by an essentially vertical cylindrical wall 29 having a diameter slightly less than that of the wall 25, so as to form a male element whose dimensions correspond approximately to the female element of the base 1. The length of this vertical cylindrical wall 29 is such that the lower face of the bottom 28 has no projection beyond this face. The lower face of the bottom 28, which is in the form of an inclined plane (see FIG. 5), has a plane peripheral crown 30 that is delimited by the vertical wall 29 and by a circular internal throat 31. The entire surface inside of the plane crown 30 has parallel longitudinal slots 32 that empty into the internal throat 31 and are delimited by parallel longitudinal ribs 33. The tops of the ribs 33 are appreciably in the same plane as the plane peripheral crown 30 so as to form an inclined upper support surface of the filtering membrane 3.

In the implementation mode shown in FIGS. 1–6, both the axial ribs 23 of the base 1 and the axial ribs 33 of the cover 2 are positioned in the same plane nd extend in the same direction as the axes of the inlet 4 and outlet 5 openings in order to facilitate the flow of the liquid to be filtered. The space formed by the circular internal throat 31 and the longitudinal slots 32 forms a chamber in contact with the upper face of the filtering membrane 3. The cover 2 also has an inlet opening 4 whose axis is, as shown in FIG. 5, parallel to the plane of the upper end 26 and which is conical in order to serve as a connection to the end of a syringe. This opening 4 passes through the wall 25 and communicates at right angles with a feed channel 34 that empties directly into the circular interior throat 31. Like channel 24, this feed channel 34 preferably has a straight section in the shape of a "U" (see FIG. 6), in which the base of the "U", the length of which can increase as the throat 31 is approached, empties into two longitudinal parallel slots 32. This particular form of the straight section, both of the channel 24 of the base 1 and of the channel 34 of the cover 2, makes it possible to mold these two pieces 1 and 2 such as with plastic without mold seams between the corresponding opening and the channel, which is very important for effecting a peridural anesthesia with complete safety, especially on the downstream side of the flow of the liquid filtered according to the invention.

As shown in FIG. 5, the filtering membrane 3, which is circular, is joined to the plane peripheral crown 30 of the cover 2 and this junction can be readily effected by automatic means from a continuous strip of filter material due to the absence of any projection beyond the lower face of the bottom 28. After the filter membrane 3 is joined on the crown 30, the base 1 is positioned and aligned on the cover 2 so that these two plastic elements, which constitute the envelope of the filtration assembly of the invention, are joined such as by employing ultrasonic energy to each other in their definitive position along the cylindrical wall 29. The materials that constitute both the filter membrane 3 and the plastic parts 1 and 2 are conventional. However, it is preferred that the filter membrane, which generally has a pore diameter of 0.1–0.5 microns, be of cellulose ester, polyolefin or polytetrafluoroethylene and that the plastic material of the envelope be of polyvinyl chloride, polyolefin or styrene-acrylonitrile resin. It should be noted that all the junctions required in the filtering assembly claimed are effected outside of the filtering surface, which makes it possible to avoid the interference of mold seams or fused material debris with the filtration. Furthermore, the path of the filtered liquid is designed to reduce to a minimum the pressure drops and obtain a mean flow rate by gravity that is greater than that obtained with the filtration assemblies used to date commercially for peridural anesthesia, with an equal surface and equal characteristics of the filtering membrane. These improved properties are obtained due to a structure that is simpler to produce because it has fewer elements that need to be welded together during assembly, more reliable in use because it retains the sensitivity necessary for the anesthetist, and more practical because it is less cumbersome and completely reversible.

I claim:

1. A filtration apparatus for peridural anesthesia comprising an envelope formed of two sections joined to each other, each section having top and bottom faces, a filter membrane positioned between said sections, each of said sections having an inlet or outlet opening that communicates with a chamber and having membrane support elements, characterized in that the membrane support elements of each of the two sections have a membrane support surface that forms an acute angle with respect to the axes of the inlet and outlet openings and that one face of one of the two membrane support surfaces includes a plane peripheral crown that is devoid of any projection beyond said peripheral crown.

2. The filtration apparatus of claim 1, characterized in that the filter membrane is welded at its periphery on said plane peripheral crown.

3. The filtration apparatus of an one of claims 1 or 2, characterized in that the acute angle formed by the membrane support surface and the axes of the inlet and outlet opening is between about 5 and 15 degrees.

4. The filtration apparatus of any one of claims 1 or 2, characterized in that the membrane support surface of at least one of the sections has longitudinal and parallel ribs extending in the direction of the axis of the inlet and outlet openings.

5. The filtration apparatus of claim 4, characterized in that at least one of the membrane support surfaces has longitudinal slots and a peripheral circular throat which forms a chamber for the flow of the liquid to be filtered through the filter membrane.

6. The filtration apparatus of any one of claims 1 or 2, characterized in that the axis of the inlet and outlet openings communicate with the corresponding chamber via a feed channel that empties directly into said chamber.

7. The filtration apparatus of claim 6 characterized in that the feed channel is perpendicular to the axis of the inlet and outlet opening.

8. The filtration apparatus of claim 7, characterized in that the feed channel that empties directly into one of the chambers, has a U-shaped section.

9. The filtration apparatus of claim 8 characterized in that the feed channel has a U-shaped section in which the base of the U empties into the peripheral circular throat of the corresponding chamber and wherein the two branches of the U empty into two longitudinal slots of the said chamber.

10. The filtration apparatus of any one of claims 1 or 2 characterized in that the acute angle formed by the membrane support surface and the axes of the inlet and outlet openings is about 10 degrees.

11. The filtration apparatus of claim 6 characterized in that the feed channel that empties directly into one of the chambers has a U-shaped section.

* * * * *